United States Patent
Myllyoja et al.

(10) Patent No.: US 11,643,616 B2
(45) Date of Patent: May 9, 2023

(54) RENEWABLE BASE OIL PRODUCTION ENGAGING METATHESIS

(71) Applicant: Neste Oyj, Espoo (FI)

(72) Inventors: Jukka Myllyoja, Porvoo (FI); Jukka Hietala, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 17/762,894

(22) PCT Filed: Sep. 25, 2020

(86) PCT No.: PCT/FI2020/050630
§ 371 (c)(1),
(2) Date: Mar. 23, 2022

(87) PCT Pub. No.: WO2021/058875
PCT Pub. Date: Apr. 1, 2021

(65) Prior Publication Data
US 2022/0340835 A1    Oct. 27, 2022

(30) Foreign Application Priority Data

Sep. 26, 2019 (FI) ..................................... 20195823

(51) Int. Cl.
*C10M 177/00* (2006.01)
*C10M 105/04* (2006.01)
(Continued)

(52) U.S. Cl.
CPC ............. *C10M 177/00* (2013.01); *C07C 6/04* (2013.01); *C07C 45/455* (2013.01); *C07C 67/03* (2013.01);
(Continued)

(58) Field of Classification Search
CPC ......... C07C 6/04; C07C 45/455; C07C 67/03; C07C 67/333; C10M 105/04;
(Continued)

(56) References Cited

U.S. PATENT DOCUMENTS 3,823,070 A   7/1974   Minato et al.
3,912,586 A   10/1975  Kaneyuki et al.
(Continued)

FOREIGN PATENT DOCUMENTS

CN   101360810 A   2/2009
CN   101868552 A   10/2010
(Continued)

OTHER PUBLICATIONS

Churi et al., "A study of metathesis of unsaturated carboxylic esters", Journal of the Oil Technologists Association of India, vol. 25, No. 4, Jan. 1, 1993, pp. 93-95.
(Continued)

*Primary Examiner* — Ellen M McAvoy
(74) *Attorney, Agent, or Firm* — Buchanan Ingersoll & Rooney PC

(57) ABSTRACT

A process is disclosed for producing renewable products, such as a renewable base oil, from a feedstock of biological origin. The process includes subjecting a feedstock containing free fatty acids and fatty acid glycerides, wherein at least one hydrocarbon chain is unsaturated, to esterification reaction in the presence of an alcohol. An ester stream thereby obtained is then subjected to metathesis conditions in the presence of a renewable alkene to obtain a metathesis product. Separation of the metathesis product includes recovery of a fraction containing or consisting essentially of C16 fatty acid esters, which is subjected to ketonisation reaction conditions to produce long chain ketones, which after hydrotreatment meet requirements for a renewable base
(Continued)

oil. Ketonisation reaction produces renewable alkene usable in metathesis reaction.

21 Claims, 3 Drawing Sheets

(51) Int. Cl.
| | |
|---|---|
| *C07C 6/04* | (2006.01) |
| *C07C 45/45* | (2006.01) |
| *C07C 67/03* | (2006.01) |
| *C07C 67/333* | (2006.01) |
| *C10G 3/00* | (2006.01) |
| *C10M 107/10* | (2006.01) |
| *C10N 20/00* | (2006.01) |
| *C10N 30/00* | (2006.01) |
| *C10N 20/02* | (2006.01) |

(52) U.S. Cl.
CPC ............ *C07C 67/333* (2013.01); *C10G 3/50* (2013.01); *C10M 105/04* (2013.01); *C10M 107/10* (2013.01); *C10G 2300/1014* (2013.01); *C10G 2300/302* (2013.01); *C10G 2400/10* (2013.01); *C10N 2020/02* (2013.01); *C10N 2020/065* (2020.05); *C10N 2030/43* (2020.05)

(58) Field of Classification Search
CPC ......... C10M 107/10; C10G 2300/1014; C10G 2300/302; C10G 2400/10
See application file for complete search history.

(56) References Cited

U.S. PATENT DOCUMENTS

| | | | |
|---|---|---|---|
| 7,256,301 B2 | 8/2007 | Erguen et al. | |
| 8,580,985 B2 | 11/2013 | Thompson et al. | |
| 8,753,853 B2 | 6/2014 | Ritter et al. | |
| 9,023,626 B2 | 5/2015 | Dubois | |
| 9,676,884 B2 | 6/2017 | Rizvi et al. | |
| 11,021,416 B2 | 6/2021 | Bosetti et al. | |
| 11,459,280 B2 | 10/2022 | Bosetti et al. | |
| 2004/0082042 A1 | 4/2004 | Staley | |
| 2005/0284940 A1 | 12/2005 | Enomoto et al. | |
| 2006/0079704 A1 | 4/2006 | Lacombe et al. | |
| 2007/0131579 A1* | 6/2007 | Koivusalmi | C10G 3/46 208/19 |
| 2007/0135663 A1 | 6/2007 | Aalto et al. | |
| 2010/0191008 A1 | 7/2010 | Olson | |
| 2010/0305354 A1 | 12/2010 | Dubois | |
| 2011/0113679 A1* | 5/2011 | Cohen | C07C 2/862 44/388 |
| 2011/0300594 A1 | 12/2011 | Ritter et al. | |
| 2012/0197032 A1* | 8/2012 | Firth | C10G 45/58 585/254 |
| 2012/0253069 A1 | 10/2012 | Zang et al. | |
| 2013/0217906 A1 | 8/2013 | Kunz et al. | |
| 2013/0225409 A1 | 8/2013 | Allen et al. | |
| 2013/0225473 A1 | 8/2013 | Allen et al. | |
| 2014/0005423 A1 | 1/2014 | Allen et al. | |
| 2014/0031592 A1 | 1/2014 | Shinde | |
| 2014/0228586 A1 | 8/2014 | Beardslee et al. | |
| 2014/0275595 A1 | 9/2014 | Wampler et al. | |
| 2015/0087521 A1 | 3/2015 | Allen et al. | |
| 2015/0210855 A1* | 7/2015 | Firth | C07C 6/04 554/163 |
| 2015/0353996 A1 | 12/2015 | Hoo et al. | |
| 2015/0361024 A1 | 12/2015 | Laplaza | |
| 2016/0251278 A1 | 9/2016 | Bosetti et al. | |
| 2016/0298145 A1 | 10/2016 | Laplaza et al. | |
| 2016/0340616 A1 | 11/2016 | Littich et al. | |
| 2017/0137365 A1* | 5/2017 | Wampler | C07C 67/08 |
| 2019/0071611 A1 | 3/2019 | Goossen et al. | |
| 2020/0181503 A1* | 6/2020 | Myllyoja | B01J 35/1061 |
| 2020/0181504 A1* | 6/2020 | Myllyoja | C10G 3/50 |
| 2020/0181527 A1* | 6/2020 | Kulmala | C10G 3/49 |
| 2021/0171420 A1 | 6/2021 | Bosetti et al. | |
| 2022/0009855 A1* | 1/2022 | Myllyoja | C11C 3/12 |
| 2022/0356131 A1 | 11/2022 | Hietala et al. | |
| 2022/0363613 A1 | 11/2022 | Hietala et al. | |

FOREIGN PATENT DOCUMENTS

| | | |
|---|---|---|
| CN | 102439118 A | 5/2012 |
| CN | 102498086 A | 6/2012 |
| CN | 102770520 A | 11/2012 |
| CN | 102781583 A | 11/2012 |
| CN | 104837802 A | 8/2015 |
| CN | 105189576 A | 12/2015 |
| CN | 106170530 A | 11/2016 |
| CN | 107001217 A | 8/2017 |
| EP | 1741768 A1 | 1/2007 |
| EP | 2155838 B1 | 9/2014 |
| ES | 2595106 T3 | 12/2016 |
| FI | 100248 B | 10/1997 |
| WO | 0017380 A1 | 3/2000 |
| WO | 0104337 A1 | 1/2001 |
| WO | 0121572 A1 | 3/2001 |
| WO | 2007068795 A1 | 6/2007 |
| WO | 2007068796 A2 | 6/2007 |
| WO | 2007068796 A3 | 8/2007 |
| WO | 2008046106 A2 | 4/2008 |
| WO | 2008048522 A1 | 4/2008 |
| WO | 2008140468 A2 | 11/2008 |
| WO | 2010068904 A2 | 6/2010 |
| WO | 2011046872 A2 | 4/2011 |
| WO | 2011056881 A2 | 5/2011 |
| WO | 2012061093 A1 | 5/2012 |
| WO | 2012129477 A1 | 9/2012 |
| WO | 2014058867 A1 | 4/2014 |
| WO | 2015108874 A1 | 7/2015 |
| WO | 2016014417 A1 | 1/2016 |
| WO | 2016062868 A1 | 4/2016 |
| WO | 2018234187 A1 | 12/2018 |

OTHER PUBLICATIONS

Ahmad, F. B. H., et al., "Co-Metathesis Reaction of Crude Palm Oil and Ethene", JAOCS, 1995, vol. 72, No. 6, pp. 757-758, AOCS Press. (2 pages).
Alm, M., "Animal Fats", 2013, AOCS Lipid Library [online]. Available at https://lipidlibrary.aocs.org/edible-oilprocessing/animal-fats [Accessed Aug. 27, 2019], (21 pages).
Bosma, R. H. A., et al., "Cometathesis of Methyl Oleate and Ethylene; a Direct Route to Methyl Dec-9-enoate", J. C. S. Chem. Comm., 1981, pp. 1132-1133. (2 pages).
Chikkali, S. et al., "Refining of Plant Oils to Chemicals by Olefin Metathesis", Angew. Chem. Int. Ed., 2012, vol. 51, pp. 5802-5808, Wiley Online Library, Wiley-VCH Verlag GmbH & Co. KGaA, Weinheim, DE. (7 pages).
Communication of Acceptance under section 29a of Patents Decree issued in corresponding Finnish Patent Application No. 20195820 by the Finnish Patent and Registration Office dated Sep. 15, 2020. (3 pages).
Communication of Acceptance under section 29a of Patents Decree issued in corresponding Finnish Patent Application No. 20195822 by the Finnish Patent and Registration Office dated Sep. 15, 2020. (3 pages).
Communication of Acceptance under section 29a of Patents Decree issued in corresponding Finnish Patent Application No. 20195823 by the Finnish Patent and Registration Office dated Sep. 15, 2020. (3 pages).
Finnish Search Report for Finnish Patent Application No. 20195823 dated Jan. 23, 2020 (3 pages).
Finnish Search Report for Finnish Patent Application No. 20195820 dated Jan. 24, 2020 (4 pages).
Finnish Search Report for Finnish Patent Application No. 20195822 dated Jan. 24, 2020 (3 pages).

(56) References Cited

OTHER PUBLICATIONS

International Search Report (PCT/ISA/210) and Written Opinion (PCT/ISA/237) dated Nov. 20, 2020, by the European Patent Office as the International Searching Authority for International Application No. PCT/FI2020/050630. (16 pages).
International Search Report (PCT/ISA/210) and Written Opinion (PCT/ISA/237) dated Nov. 20, 2020, by the European Patent Office as the International Searching Authority for International Application No. PCT/FI2020/050631. (16 pages).
International Search Report (PCT/ISA/210) and Written Opinion (PCT/ISA/237) dated Dec. 16, 2020, by the European Patent Office as the International Searching Authority for International Application No. PCT/FI2020/050632. (17 pages).
Lee, H. et al., "Biotransformation of dicarboxylic acids from vegetable oil-derived sources: current methods and suggestions for improvement", Applied Microbiology and Biotechnology, 2019, vol. 103, pp. 1545-1555. (11 pages).
Mandelli, D. et al., "Ethenolysis of Esters of Vegetable Oils: Effect of B2O3 Addition to Re2O7/SiO2.Al2O3-SnBu4 and CH3ReO3/SiO2.Al2O3 Metathesis Catalysts", JAOCS, 1996, vol. 76, No. 2, pp. 229-232, AOCS Press. (4 pages).
Metzger, J. O., "Fats and oils as renewable feedstock for chemistry", Eur. J. Lipid Sci. Technol., 2009, vol. 111, pp. 865-876. (13 pages).
Millican, R. C., et al., "The Isolation and Properties of Some Naturally Occurring Octadecenoic (Oleic) Acids", J. Biol. Chem., 1944, vol. 154, pp. 437-450. (15 pages).
Mobley, D. P., "Biosynthesis of Long-Chain Dicarboxylic Acid Monomers From Renewable Resources—Final Technical Report", DE-FC36-95G010099, Apr. 1999 (178 pages).
Mol, J. C., et al., "Metathesis in Oleochemistry", J. Braz. Chem. Soc., 1998, vol. 9, No. 1, pp. 1-11, Soc. Bras. Química. (11 pages).
Spekreijse, J., et al., "The Future of Ethenolysis in Biobased Chemistry", ChemSusChem, 2017, vol. 10, pp. 471-482, Wiley Online Library, Wiley-VCH Verlag GmbH & Co. KGaA, Weinheim, DE. (13 pages).
Warwel, S., et al., "Polymers and surfactants on the basis of renewable resources", Chemosphere, 2001, vol. 43, pp. 39-48, Elsevier Science Ltd. (10 pages).
Watthanasringkarn, S., et al., "Synthesis of Lubricant from Methyl Ester Palm Stearin", Int'l Journal of Research in Chemical, Metallurgical and Civil Eng., 2015, vol. 2, No. 1, pp. 9-12. (4 pages).
Wheeler, D. H., et al., "The Preparation and Properties of Highly Purified Methyl Oleate", Oil and Soap, Nov. 1939, vol. 16, No. 11, pp. 207-209. (3 pages).
Woo-Young, Jeon, et al.., "Microbial production of sebacic acid from a renewable source production, purification, and polymerization", Green Chemistry, vol. 21, No. 23, Jan. 2019, pp. 6491-6501. (11 pages).
Wyrębek, P. et al., "Looking for the Noncyclic(amino)(alkyl)carbene Ruthenium Catalyst for Ethenolysis of Ethyl Oleate: Selectivity is on Target", ACS Omega, Dec. 27, 2018, vol. 3, pp. 18481-18488, ACS Publications. (15 pages).
Office Action dated May 11, 2022, by the Canadian Patent Office in corresponding Canadian Patent Application No. 3,149,520. (4 pages).
Office Action (Notice of First Office Action) dated Oct. 19, 2022, by the Chinese Patent Office in corresponding Chinese Patent Application No. 202080066686.8, and an English Translation of the Office Action. (19 pages).
Office Action (Notice of First Office Action) dated Oct. 31, 2022, by the Chinese Patent Office in corresponding Chinese Patent Application No. 202080066719.9, and an English Translation of the Office Action. (17 pages).
Office Action dated Oct. 12, 2022, by the U.S Patent and Trademark Office in U.S. Appl. No. 17/762,974. (13 pages).
Office Action dated Sep. 21, 2022, by the U.S. Patent and Trademark Office in U.S. Appl. No. 17/762,893 (6 pages).
Office Action dated Dec. 14, 2022, by the Chinese Patent Office in corresponding Chinese Patent Application No. 202080066687.2, and a machine English Translation of the Office Action. (16 pages).
Office Action dated Feb. 6, 2023, by the U.S. Patent and Trademark Office in U.S. Appl. No. 17/762,893.

\* cited by examiner

RENEWABLE BASE OIL PRODUCTION ENGAGING METATHESIS

FIELD OF THE INVENTION

The present disclosure relates to a process for producing various hydrocarbon products, such as renewable base oil. In particular the process includes metathesis reaction of an unsaturated fatty acid ester with an alkene. Further, herein is provided a method relating to more efficient biomass utilisation in base oil production through utilisation of the C=C double bonds naturally occurring in the feedstock. The present disclosure relates to renewable base oil production, wherein further products obtained may comprise renewable chemicals.

BACKGROUND OF THE INVENTION

Renewable feedstocks present a sustainable alternative to petrochemical sources. The renewable feedstocks have been derived from e.g. variety of vegetable oils, animal fats, recycled waste oils and even microbial oils. Hydrotreated vegetable oils such as palm oil, derivatives thereof, animal fat and other wastes or residues have been the major feedstock dominating the global renewable fuel market. The present process is related to producing renewable base oil from the same or closely similar feedstocks of biological origin.

Hydrotreating is an efficient process, but when applied to feedstock originating from renewable materials, it does not utilize the natural characteristics of the feedstock in the most elegant way. For example, reduction of triglycerides into paraffinic hydrocarbons involves saturation of C=C double bonds and loss of all oxygen containing functionalities even though they could be useful and valuable in certain other product fractions. Therefore, there is a need for more sophisticated overall processes, wherein feedstock is utilized more efficiently and feedstock characteristics are better taken into consideration. Further, there is a need for avoiding excessive hydrogen consumption. Yet, there still is a need to minimize possible oxygen-containing high value compounds ending up in lower value hydrocarbon products.

Metathesis was first reported in the literature two decades ago. Since then, is has been studied for various compounds and corresponding results published. It has been suggested to use alkene metathesis to convert oleochemicals into value-added products such as the bifunctional molecule methyl-9-decenoate. However, low ethenolysis efficiency and a need for peroxide-scavenging feedstock pretreatment have decreased the overall interest.

One example of published metathesis reports is an international patent application publication WO2008046106 A2. It aims at a process for producing terminal alkenes from internal alkenes, especially from a variety of olefinic sources. In the experimental part it studies the reactions referred to as ethenolysis, propenolysis and butenolysis using soy FAME as a model material. The reactions were followed as methyl-9-decenoate turnover. Even though the alkene is of renewable origin, the reagents used therein are not.

US 2015210855 A1 is another document concerning metathesis, but focused specifically on high-weight olefin, ester and acid production. High-weight products refer to C25+, C25-C100, or C25-C36 ranges.

Renewable base oil can be produced for example by a process described in EP06820127. It discloses producing a hydrocarbon component, and particularly a high-quality saturated hydrocarbon base oil of biological origin, through a sequence of a ketonisation step, a hydrodeoxygenation (HDO) step and an isomerisation step. Isomerisation of fatty acids and fatty acid alkyl esters is performed prior to the ketonisation step, whereas the isomerisation of paraffins is carried out following the ketonisation and HDO steps.

Another document disclosing production of a renewable base oil by ketonisation from glyceride containing feedstocks, is US 2007135663 A1. Two molecules of fatty acids react in a ketonisation reaction to produce long-chain ketones, which are consequently converted to paraffins directly, or via hydrogenation of eventual double bonds. In example 3, methyl esters are used instead of carboxylic acids in ketonisation. However, it does not disclose a combination of ketonisation with metathesis.

Hence, there is a need for a process for base oil production, preferably combined base oil and alkene production from a glyceride containing feedstock. Further, there is a need to improve metathesis efficiency. Further, there is a need to use the feedstock efficiently, such as by producing further products in addition to metathesis products.

SUMMARY OF THE INVENTION

To overcome at least some of the problems of the prior art, herein is provided a novel process for producing renewable base oil, said process comprising the steps of a) providing the glyceride containing feedstock comprising free fatty acids, fatty acid glycerides selected from monoglycerides, diglycerides and triglycerides of fatty acids, or a mixture thereof, wherein the feedstock contains a compound having at least one carbon-carbon double bond;

b) subjecting the feedstock to esterification reaction, preferably selected from esterification of fatty acids and transesterification of mono- di- or triglycerides or a combination thereof, in the presence of a C2-C4 monoalcohol, to yield a fatty acid ester containing stream;

c) subjecting said fatty acid ester containing stream to metathesis reaction conditions in the presence of a C2-C4 alkene to obtain a product comprising a mixture of alkenes and fatty acid esters, d) subjecting the product from step c) to separation to provide at least a first fatty acid ester fraction comprising saturated fatty acid esters having a carbon chain length of C16 in an amount of at least 80%-wt of the total fraction weight;

e) subjecting the first fatty acid ester fraction to ketonisation to yield C2-C4 alkene, preferably ethene, and a ketonisation product comprising a C31 ketone;

f) recycling the C2-C4 alkene, preferably ethene, from step e) to metathesis reaction in step c);

g) subjecting the ketonisation product of step e to hydrotreatment to obtain renewable base oil fulfilling the API Group III base oil specifications, having ≥90 wt % saturated hydrocarbons, ≤0.03 wt % sulfur and a viscosity index of ≥120.

The present inventors have found that a glyceride containing feedstock comprising free fatty acids, fatty acid glycerides selected from monoglycerides, diglycerides and triglycerides of fatty acids, or a mixture thereof can be refined to renewable base oil meeting the API Group III base oil specifications with improved efficiency when metathesis reaction is used to react unsaturated moieties into further products. Unexpected synergy has been found when the renewable C2-C4 alkene released during ketonisation is recycled back and used as metathesis reagent, thus decreasing or even removing the need for fresh alkene introduction into the metathesis process.

As explained in detail below, further advantages are obtainable through other embodiments of the processes and uses.

BRIEF DESCRIPTION OF THE DRAWINGS

The invention will be described in more detail by means of preferred embodiments. Reference is made to the following figures, in which.

DETAILED DESCRIPTION OF THE INVENTION

Figure 1:
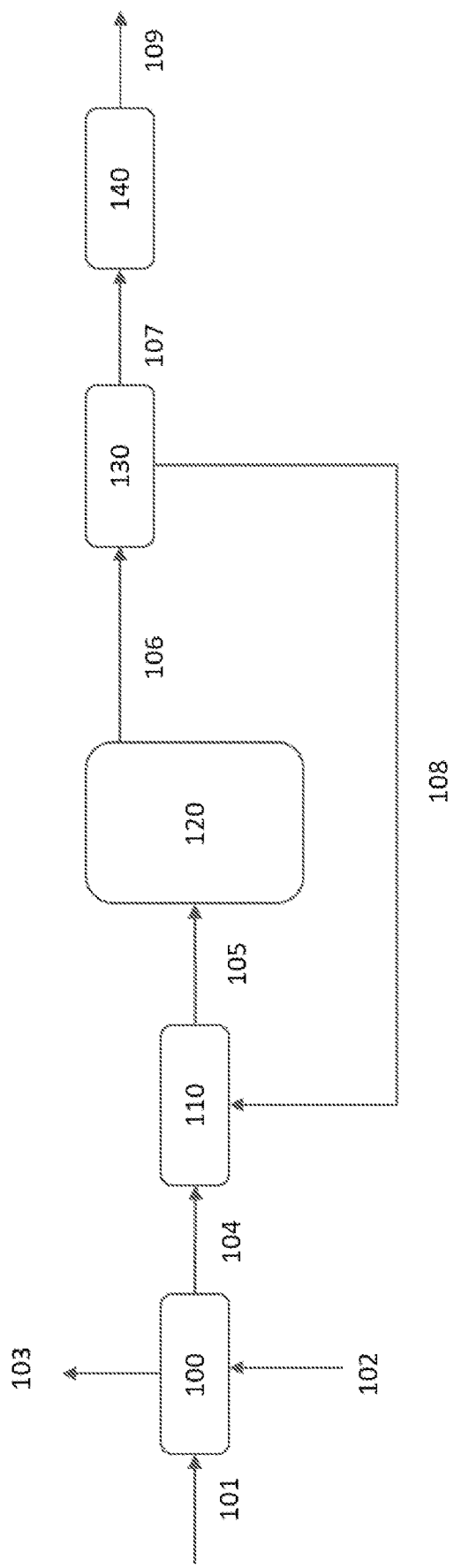
FIG. 1 shows a schematic arrangement of an embodiment of the present process as a flowchart following the stepwise structure of the process of claim 1.

The present disclosure provides process for producing at least renewable base oil from a glyceride containing feedstock.

The Glyceride Containing Feedstock

The feed to the present process is here defined as glyceride containing feedstock. The glyceride containing feedstock comprises free fatty acids, fatty acid glycerides selected from monoglycerides, diglycerides and triglycerides of fatty acids, or a mixture thereof. It is essential for the metathesis process that the feedstock contains a compound, in practice compounds, having at least one carbon-carbon double bond. Glyceride containing feedstocks are of biological origin. Biological fats and oils originating from plants, animals or fishes are naturally in form of glycerides, hence fatty acids are present as glycerol esters.

The glyceride containing feedstock suitable for the process and use according to the present invention comprises free fatty acids and glycerides. Particularly suitable glyceride containing feedstocks for renewable base oil production, are those which comprise glycerides abundant with palmitic acid moieties, i.e. C16 fatty acid esters. In addition, the feedstock contains compounds having at least one carbon-carbon double bond, such as unsaturated fatty acid moieties. Typically, the feedstock further comprises C18:1 fatty acid moieties.

Several oils and fats contain significant amounts of C16 fatty acids. Partly the fatty acids are already in the form of free fatty acids (FFA), but partly they are bound to glycerin as esters.

Table 1 lists availability of some C16 and C18 free fatty acids from natural material sources, and the fatty acid carbon chain lengths and unsaturation of exemplary fats and oils found in the literature, possibly suitable for use in the process of the present invention.

TABLE 1

Exemplary glyceride containing feedstocks suitable for the process for producing renewable base oil of the present invention.

| | The fatty acid distribution of glyceride containing feedstocks suitable for the present process (%-wt) | | | | | | | | | | | | | Amount of FFAs |
|---|---|---|---|---|---|---|---|---|---|---|---|---|---|---|
| Fat/oil | 8:0 | 10:0 | 12:0 | 14:0 | 16:0 | 18:0 | 18:1 | 18:2 | 18:3 | 20:0 | 20:1 | 22:0 | 22:1 | [2]Amount of C16 and C18 FFAs |
| Canola | | | | 0.1 | 4.1 | 1.8 | 60.9 | 21.0 | | 0.7 | | 0.3 | | |
| Crude tall oil | | | | | [1]1-2 | | | | | | | | | |
| Cottonseed | | | | 0.7 | 21.6 | 2.6 | 18.6 | 54.4 | 0.7 | 0.3 | | 0.2 | | |
| Crumbe | | | | | 1.7 | 0.8 | 16.1 | 8.2 | 2.9 | 3.3 | | 2.2 | 59.5 | |
| Cuphea (PSR-23) | 0.8 | 81.9 | 3.2 | 4.3 | 3.7 | 0.3 | 3.6 | 2.0 | 0.3 | | | | | |
| Jatropha | | | | | [1]15 | | | | | | | | | 1.5-5 |
| Palm | | | 0.2 | 1.1 | 44.0 | 4.5 | 39.1 | 10.1 | 0.4 | 0.4 | | | | 4-7 |
| Palm Kernel | 3.3 | 3.4 | 48.2 | 16.2 | 8.4 | 2.5 | 15.3 | 2.3 | | 0.1 | 0.1 | | | |
| Palm stearin | | | | | [1]60 | | | | | | | | | 0.1 |
| PFAD | | | | | [1]45 | | | | | | | | | 75-88 |
| Rapeseed | | | | | 2.7 | 1.1 | 14.9 | 10.1 | 5.1 | 10.9 | | 0.7 | 49.8 | |
| Soybean | | | 0.1 | 0.2 | 10.7 | 3.9 | 22.8 | 50.8 | 6.8 | 0.2 | | | | 2.5 |
| Sunflower | | | | | 3.7 | 5.4 | 81.3 | 9.0 | | 0.4 | | | | 0.5 |
| Lard | | 0.1 | 0.1 | 1.5 | 26.0 | 13.5 | 43.9 | 9.5 | 0.4 | 0.2 | 0.7 | | | 5-10 |
| Tallow | | | | 0.1 | 3.2 | 23.4 | 18.6 | 42.6 | 2.6 | 0.7 | 0.2 | 0.3 | | 5-10 |

[1]Values measured at the Analytics lab of Neste Oyj by GC.

[2]Estimation of C16-C18 FFAs in %-wt is based on ½ * TAN (total acid number analysis), which is a fair approximation.

Typical basic structural unit of plant and fish oils and animal fats is a triglyceride. Triglyceride is an ester of glycerol with three fatty acid molecules having the structure below:

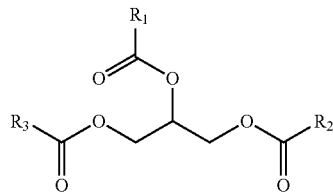

wherein $R_1$, $R_2$ and $R_3$ ($R_x$) are the same or different and represent saturated or unsaturated C3-C27 hydrocarbon chains. The length of the hydrocarbon chain for $R_x$ is typically 17 carbons they are referred to as C18 fatty acids. Another typical length of the hydrocarbon chain for $R_x$ is 15 carbons with reference to C16 fatty acids. In general, typical carbon numbers of the fatty acids linked to the two other hydroxyl groups are even, being generally between carbon chain lengths from C12 to C22.

In addition to the prevailing triglycerides, some diglycerides and monoglycerides may be present as well. Diglycerides are esters of glycerol with two fatty acid molecules having alkyl groups $R_x$ and monoglycerides are ester of glycerol with one fatty acid molecules having an alkyl group $R_x$ bound therein. These mono- and diglycerides release glycerol in hydrolysis as well. Mono- and diglycerides are formed in minor amounts spontaneously from triglycerides during storage or under purification conditions, releasing some free fatty acids. Hence, the term as used herein "glyceride containing feedstock" means feed comprising mono-, di-, triglycerides and/or free fatty acids.

Prior to processing, the glyceride containing feedstock of biological origin should be purified with suitable known methods, such as thermally, mechanically for instance by means of shear force, chemically for instance with acids or bases, or physically with radiation, distillation, cooling, or filtering. The purpose of chemical and physical purifications is to remove impurities interfering with the process or poisoning the catalysts, and to reduce unwanted side reactions. Hence, according to one embodiment, the glyceride containing feedstock is subjected to purification before entering into the esterification reaction step. This purification may include e.g. degumming, bleaching and/or deodorizing.

Thus, glyceride containing feedstocks suitable for the process of the present invention comprise mono- di- and/or triglycerides and free fatty acids. Exemplary glyceride containing feedstocks are plant fats, plant oils, plant waxes, animal fats, such as lard, tallow, yellow grease, brown grease, animal oils, animal waxes, fish fats, fish oils, and fish waxes. Preferably, the glyceride containing feedstock material originates from waste and/or residues of the mentioned exemplary glyceride containing feedstocks. More preferably, the waste and/or residues originate from sustainably-produced products, the production routes of which are traceable. Preferable feedstocks of animal origin are discussed in detail by Alm, M, (2013) Animal fats. [online]. Available at https://lipidlibrary.aocs.org/edible-oil-processing/animal-fats [Accessed 27 Aug. 2019].

According to a specific embodiment, the "glyceride containing feedstock" comprises PFAD or consists of PFAD. PFAD (palm oil fatty acid distillate) is a processing residue from the refining of food-grade palm oil for the food industry uses. PFAD is considered as a waste or residue raw material.

When oil palm fruits are handled, normal bruising occurs causing the fat in the fruit to start degrading. The longer it takes for the fruit to be transported, processed, and refined into palm oil, the larger part of the fats degrade. When palm oil is being refined into food grade oil, these degraded fats, free fatty acids, are removed from the oil by distilling to improve taste, odor, and color of the oil, as well as to increase the shelf life. PFAD consists of these degraded fats that are undesired for food production and need to be removed during the palm oil refining process before the oil meets the food industry's quality standards. PFAD as a by-product of physical refining of crude palm oil products is typically composed of free fatty acids (e.g. 81.7%), glycerides (e.g. 14.4%), squalene (0.8%), vitamin E (0.5%), sterols (0.4%) and other substances (2.2%). The composition may vary depending on i.e. geographical location of the raw material, growth conditions and the refining process.

When the appropriate glyceride containing feedstock, optionally after purification, is provided in step a, the next step, step b of the present process esterifies or transesterifies it to fatty acid esters.

Esterification Reaction

The feedstock as defined above, is subjected to esterification reaction. Esterification reaction may comprise esterification of fatty acids in the presence of a C2-C4 monoalcohol to yield a fatty acid ester containing stream. When glycerides are present in the feedstock, this step comprises a transesterification of mono- di- or triglycerides or a combination thereof, in the presence of a C2-C4 monoalcohol to yield a fatty acid ester containing stream.

As used herein, references to carbon numbers of fatty acid esters disregard the carbon number of the residue originating from the alcohol. For example, ethyl palmitate ($C_{18}H_{36}O_2$) is referred to as C16 fatty acid ester or C16 fatty acid ethyl ester, hence an ester wherein the fatty acid residue carbon chain length is C16 and the two other carbons originate from ethanol. The glyceride containing feedstock is esterified before subjecting it to metathesis step. This is due to sensitivity of the metathesis reaction, wherein free fatty acids are not an optimal feed. Triglycerides as feed to metathesis are not ideal either, because their higher viscosity slows down the reaction rate and their complex structure produces a high variety of products leading to complicated separations.

Transesterification is a process well known in the art, i.e. for production of biodiesel, such as FAME (fatty acid methyl esters). Glycerides are reacted in the presence of an alcohol to fatty acid esters. A common alcohol is methanol, producing fatty acid methyl esters (FAME). If ethanol is used in transesterification, fatty acid ethyl esters (FAEE) are obtained. Catalysts suitable for such reactions are known in the art. Hence, the ester bonds between glycerol and fatty acids are cleaved releasing glycerol, but the fatty acid residues are still in form of esters. The separation of glycerol from fatty acid esters formed is known in the art. Glycerol may be further reacted to useful compounds, such as propane diols or propanols.

In the present process, the monoalcohol used for esterification reaction of step b is selected from C2-C4 alcohols, hence, ethanol, 1-propanol, 2-propanol, 1-butanol and 2-butanol, or a mixture thereof, preferably from bio-based monoalcohols. Monoalcohol refers to alcohol comprising only one hydroxyl group. Bio-based ethanol is abundantly available from fermentation of sugars and carbohydrates. Biobased propanols may be obtained from e.g. glycerol. The common alcohol for transesterification, methanol is not applicable in the present process. Methyl esters fail to provide the synergistic advantages to the overall process since they do not produce alkenes in ketonisation reactions.

In one embodiment ethanol in esterification reaction and ethene in metathesis correspondingly are used. Preferably, the ethanol is bioethanol.

In another embodiment a propanol, 1-propanol or 2-propanol, in esterification reaction and propene in metathesis are used. Preferably, the propanol is biopropanol, hence originating from non-fossil feedstock. Such uses are advantageous to the overall process and contribute to character of metathesis products as 100% renewable.

Esterification reaction provides an advantage in transforming the glyceridic structures, possibly comprising up to three ester bonds, hence triesters and molecular weight typically about 700-900 g/mol, into smaller and simpler monoesters, the reactions and products of narrower variation in the following process steps.

As a specific embodiment, the glyceride containing feedstock may be subjected to splitting, preferably hydrolysis, before said esterification reaction. In said splitting, glycerol and free fatty acids or fatty acid salts are released from mono-, di- and triglycerides. Possible fatty acid salts are converted to free acids before or during the esterification. Free fatty acids are then esterified. Combination of hydrolysis and esterification is an alternative to transesterification. Esterification of free fatty acids is preferably catalytic, carried out over homogenous or heterogenous catalysts, such as a zinc laurate or a zinc stearate catalyst.

Optional Pretreatment Methods Prior to Metathesis

Depending on the feedstock quality, the feedstock to the metathesis reaction may be pretreated when required. These pretreatments include possible removal of alcohols and peroxides.

Alcohols are optionally removed before feeding fatty acid esters to the metathesis reaction. According to an embodiment, the overall process according to the present invention comprises at least one pretreatment step between steps b and c. Such pretreatment step comprises treatment with an adsorbent, with a metal alkyl compound, with a metal alkoxide compound, with a reducing agent or with an organic drying agent, a thermal treatment or a combination thereof.

Some metathesis catalysts are known to be sensitive to impurities. With high catalyst loadings, catalyst poisoning is not immediately observed. However, at the lower limit of catalyst loading, the relative concentration of trace impurities to catalyst becomes larger and activity suffers. One typical class of impurities is organic hydroperoxides, which can be formed in natural oils by oxidative ageing.

The fatty acid alkyl esters may be treated with the magnesium silicate, such as commercially available Magnesol. It has been reported to improve metathesis efficiencies at low catalyst loadings. Another pretreatment option is triethylaluminium treatment alone or together with further compounds, such as $Ac_2O$. Yet another chemical pretreatment method comprises treatment with metal alkoxides, such as $Al(iPrO)_3$ and $Zr(OEt)_4$. As physical treatment for peroxide removal heating the feedstock to a temperature greater than 100° C. in the absence of oxygen may be used.

A combination of chemical and physical pretreatments may comprise for example thermal treatment together with an absorbent treatment.

Metathesis

The fatty acid ester containing stream obtained from esterification reaction is next subjected to metathesis reaction conditions in the presence of a C2-C4 alkene. The metathesis is an equilibrium reaction producing variable products, hence from metathesis, a mixture of alkenes and fatty acid esters is obtained as product.

Metathesis reaction is based on rearrangements around C=C double bonds of two molecules of starting materials. The present application of metathesis aims at producing shorter alkenes and esters from unsaturated fatty acid esters. This is achieved by reacting the unsaturated fatty acid esters with a short chain alkene, such as a C2-C4 alkene. Depending on the alkene used, the length of the unsaturated fatty acids and the double bond position(s) therein, a metathesis reaction between these components produces a mixture comprising C5-C12 alkenes and C6-C18 unsaturated esters. Saturated compounds, such as palmitic acid esters, act as inerts and pass through metathesis reaction unreacted.

As recommended by IUPAC, alkene is used here to denote an unsaturated hydrocarbon that contains at least one carbon—carbon double bond. Carbon-carbon double bond, or C=C-bond is also referred to as olefinic bond. In some contexts, such as in reference to poly alpha olefins, olefin is used herein as synonym to alkenes.

Metathesis is conducted at a temperature from 20 to 120° C., a pressure from 0.1 to 3 MPa using at least one metathesis catalyst.

The metathesis reaction can be catalyzed by one or more metathesis catalysts. Typically, fatty ester metathesis catalysts are homogeneous. In case they can catalyze side reactions in successive reaction steps, it is advantageous to remove them from the solution after metathesis. A non-limiting description of suitable metathesis catalysts include complexes of the type I and II:

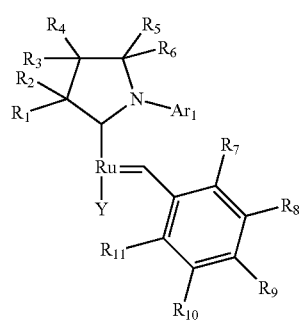

wherein:

$R_1$-$R_6$=same or different and selected from H, alkyl, cycloalkyl, alkenyl, aryl;

$Ar_1$=phenyl or benzene ring substituted with alkyl, cycloalkyl, alkenyl, Cl, Br, $OR_{12}$ ($R_{12}$=H, alkyl) or an aryl;

$R_7$-$R_{11}$=same or different and selected from H, alkyl, cycloalkyl, alkenyl, aryl, Cl, Br, $NO_2$, $OR_{13}$ ($R_{13}$=H, alkyl), $CH_2NR_{14}R_{15}$ ($R_{14}$, $R_{15}$=alkyl, benzyl, aryl); Y=N $R_{16}$ $R_{17}$ ($R_{16}$, $R_{17}$=alkyl, benzyl, $CH_2$-aryl), $OR_{18}$ ($R_{18}$=alkyl).

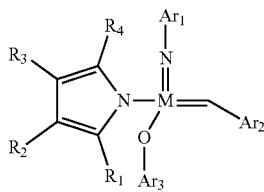

II wherein M=Mo or W;
R$_1$-R$_4$=same or different and selected from H, alkyl, cycloalkyl, alkenyl, aryl, Cl, Br, OR' (R'=H, alkyl);
Ar$_1$, Ar$_2$, Ar$_3$=same or different and selected from phenyl or benzene substituted with alkyl, cycloalkyl, alkenyl, Cl, Br, OR" (R"=H, alkyl) or an aryl.

In prior art, carbene complex metathesis catalysts comprising a group 8 transition are reported. Said transition metal is preferably selected from ruthenium, molybdenum, osmium, chromium, rhenium, tungsten. Alkene in high purity, typically >99%-vol is fed to metathesis reactor preferably in excess, to avoid self-metathesis of the feed components. Such catalysts are needed in low quantities, for example less than 150 ppm, less than 10 ppm or less than 5 ppm, for Ru catalysts, even from 2 to 4 ppm by weight, as calculated against the fatty acid ester fraction weight fed to metathesis. Catalyst quantity is optimized based on mass transfer to provide to the catalyst continuously more unreacted fatty acid esters and metathesis reagent than metathesis products.

Metathesis is a reaction between two compounds having at least one C=C double bond each. In the present process, metathesis is used for cutting fatty acid structures having carbon numbers typically C18, to molecules having lower carbon numbers with the aid of C2-C4 alkenes, hence shortening of said fatty acid structure. Hence, the C2-C4 alkenes are considered here as metathesis reagents and used in excess. The metathesis reagent may be selected from ethene, propene and butenes (1-butene and 2-butene). Ethene and 2-butene provide advantages through their symmetry, which results in lower product variation. To enable good control of the reactions, typically only one type of an alkene is selected at a time. The alkene in step c is the same C2-C4 alkene as in step e), the preferred C2-C4 alkene is ethene.

It is considered especially advantageous to use renewable C2-C4 alkene, thus renewable C2 alkene, C3 alkene or C4 alkene or a combination thereof, as reagent for metathesis reaction. This is now surprisingly possible through combination of a metathesis reaction with a ketonisation reaction releasing renewable alkenes in the same overall process. Accordingly, the C2-C4 alkene recovered from a ketonisation reaction of fatty acid ethyl esters is recycled and used as a reagent in the metathesis reaction, preferably according to the multistep process for producing renewable base oil according to the present disclosure.

This can be exemplified with ethene. According to an embodiment, where ethene is used as the metathesis reagent, it originates from renewable ethanol esterified to fatty acids in esterification or transesterification reaction. In ketonisation reaction between two fatty acid ethyl esters, such as two ethyl palmitates, a C31 ketone and renewable ethene originating from said ethanol, are formed. This ethene can be recycled back to the metathesis reaction. Producing the ethene reagent in the same process where it is used as reagent enables on-demand production and avoidance of reagent storage. Further, ethene recovered through flash or evaporation after metathesis reaction is preferably recycled back to metathesis reaction. As understood, corresponding system may be implemented with a C3 alkene or a C4 alkene.

In embodiments using ethene as reagent, the main reaction taking place is formation of 1-decene and ethyl-9-decenoate, 9-DAEE from ethyl oleate and ethene. Side reactions produce C6-C12 linear alpha olefins and C13-C24 esters. The metathesis reactions are equilibrium reactions and run accordingly. Shorter alkenes form from reactions of polyunsaturated C18:2 and C18:3 with ethene. An example is given in Scheme 1 illustrating the chain shortening in metathesis reaction.

Scheme 1. Example of metathesis reaction of ethyl oleate and ethene producing 1-decene and ethyl-9-deceoate.

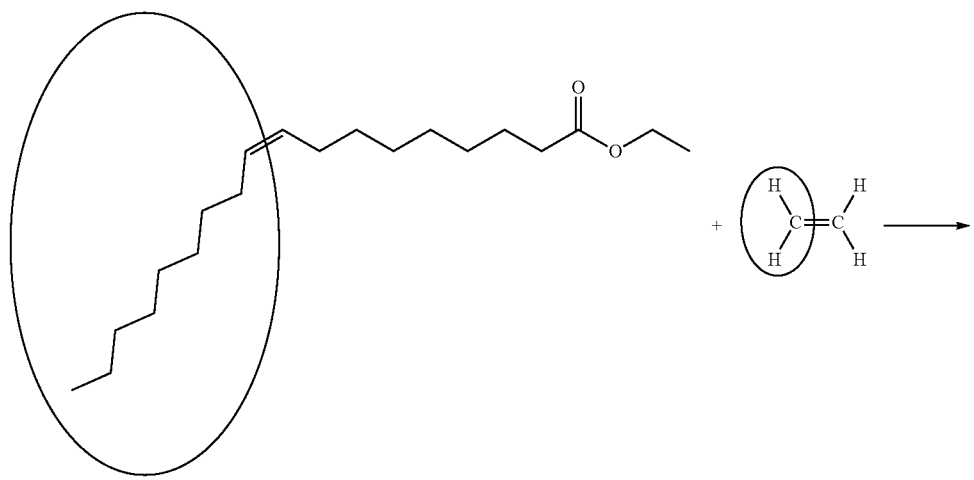

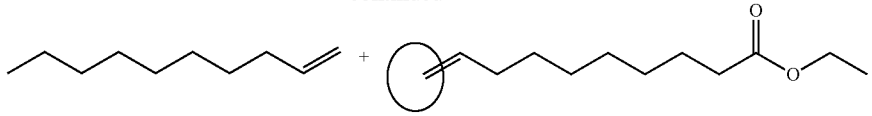

Regarding the desired products, palm oil or palm oil fatty acids provide an advantageous feed. PFAD is especially rich in oleic acid. Metathesis reaction between oleic acid ethyl ester and ethene produces 1-decene and ethyl-9-decenoate. Of these, 1-decene is particularly attractive as a component for polyalphaolefin (PAO) production which again may be used for lubricant manufacture. Among other unsaturated C10-C15 fatty acid esters, ethyl-9-decenoate is an interesting precursor chemical for refining into oleochemicals.

As initial step, the C2-C4 alkenes may be removed from the reaction mixture by evaporation, such as flash evaporation. The majority of this evaporate comprises the reagent used in excess in the metathesis reaction, which may optionally be recycled back to metathesis reaction from evaporation. Removal of said light alkenes enables recycling and provides better control for the following separation step, wherefrom products are recovered.

Fractionation of the light alkene depleted metathesis products is conducted by separation, preferably by fractional distillation. Some C5-C9 alkenes are recovered as alkene product, of which the major fraction, the C5-C7 alkenes, may be directed to renewable naphtha production.

As main product fractions, 1-decene and shortened esters, such as 9-DAEE are recovered from said separation. When recovered from the present process, 1-decene is obtained in high purity, preferably over 99 w-%. It may further be reacted by polymerisation to renewable (bio-PAO) suitable for lubricant applications. 9-DAEE fraction recovered from the distillation is also of high purity, preferably over 98 w-%. It finds uses in manufacturing polymers, surfactants and/or solvents.

Separation (Step d)

Metathesis products are recovered by the separation in step d. A specifically useful separation process comprises fractional distillation. Fractional distillation separates the metathesis products providing streams suitable for different further processes. Such procedure enables tailoring the process controls for each stream specifically, and helps avoiding suboptimal conditions and formation of side products. In addition to the first fatty acid ester fraction comprising saturated fatty acid esters having a carbon chain length of C16 in an amount of at least 80%-wt of the total fraction weight further fractions are preferably recovered. Hence, the separation in step d may provide at least one further fraction selected from

- a fraction comprising or consisting essentially of C10-C12 alkenes,
- a second fatty acid ester fraction comprising or consisting essentially of unsaturated fatty acid esters having a carbon chain length of C10-C12,
- a third fatty acid ester fraction comprising or consisting essentially of fatty acid esters having a carbon chain length of C18-C20, and
- a bottom product Embodiments of the present process provide advantages over prior art processes through sophisticated use of these fractions.

Ketonisation

Ketonisation reaction is an excellent deoxygenation reaction when deoxygenation, stability and energy density of products are the targets, as is often the case in production of fuels and base oils. Ketonisation removes 75 mol-% of the oxygen bound to carboxylic acid molecules without use of hydrogen. During the ketonisation reaction two fatty acid ester molecules are reacted together forming the corresponding linear ketone. One molecule of $CO_2$ and water is simultaneously released during the reaction.

Ketonisation reaction may be carried out with high conversion, such as 95%, or 98%, or even 99.9%, and with excellent selectivity, such as 85%, or 92%, or even 95%, which is the reason why the renewable base oil yield can be almost theoretical. Due to the very selective ketonisation reaction only few or no light hydrocarbons are formed, therefore, bio-$CO_2$ recovered from the ketonisation reaction can be very pure, preferably at least 99% by volume, and it can be used for varying applications. Naturally, the ketones produced from the fatty acid fractions obtained by the process of the present invention may also be used as chemicals for various applications other than base oil or fuel component production.

Ketonisation conditions are typically specified by the reactor temperature and pressure, the used catalyst, the carrier gas/feed ratio and weight hourly space velocity of the feed. The selected ranges may be combined according to need depending on the parameters to be optimized.

Ketonisation of the First Fraction

In the present process, a first fatty acid ester fraction comprising saturated fatty acid esters having a carbon chain length of C16 in an amount of at least 80%-wt of the total fraction weight is subjected to ketonisation. Ketonisation product obtained from this reaction yields a product mixture that comprises or consists essentially of C31 ketone. It is advantageous that the amount of said C31 ketone is at least 50%-wt, preferably at least 60%-wt, more preferably at least 70%-wt of the liquid product mixture weight.

It is characteristic to the present process that the fatty acid esters subjected to ketonisation are saturated. This provides advantages first in the ketonisation, wherein the carbon-carbon double bonds do not interfere with ketonisation reactions. Prehydrogenation needed in some prior art processes prior to ketonisation can also be avoided. Further, when the ketonisation product is hydrotreated, carbon-carbon double bonds are known to participate said reactions and lead to formation of cyclic structures to the product paraffins. With saturated fatty acid esters in the ketonisation, the product thereby obtained is more homogenous and the cycloparaffins avoided in the base oil thus produced.

In the present invention, the ketonisation reaction may be carried out at a reaction temperature ranging from 300 to 400° C., more preferably from 330 to 370° C., most preferably from 340 to 360° C. The pressure range may be from from 0.5 to 3.0 MPa, more preferably from 1.0 to 2.5 MPa, most preferably from 1.5 to 2.0 MPa, in the presence of ketonisation catalyst. A suitable ketonisation catalyst comprises one or more metal oxide catalysts, preferably the metal of the metal oxide catalyst is selected from one or more of Na, Mg, K, Sc, Fe, Co, Ni, Cu, Zn, Sr, Y, Zr, Mo, Rh, Cd, Sn, La, Pb, Bi, Ti, Mn, Mg, Ca, Zr and rare earth metals. More preferably, the ketonisation catalyst is a metal oxide catalyst selected from the list consisting of one or more of: Ti, Mn, Mg, Ca, and Zr containing metal oxide catalyst. Most preferably, the catalyst is Ti containing metal oxide catalyst, such as $K_2O/TiO_2$ catalyst, or $TiO_2$ containing catalyst, such as $TiO_2$ catalyst. The weight hourly space velocity (WHSV) may be in the range from 0.25 to 3.0 h–1, preferably from 0.5 to 2.0 h–1, more preferably from 1.0 to 1.5 h–1. Ketonisation reaction may be performed in the presence of a gas in the range from 0.1 to 1.5 gas/feed ratio (w/w), preferably from 0.25 to 1.0, most preferably from 0.5 to 0.75, wherein the gas/feed ratio (w/w) means the mass of gas fed into the ketonisation reactor per the inlet fatty acid mass of the liquid feed into the ketonisation reactor. The gas is selected from one or more of: $CO_2$, $H_2$, $N_2$, $CH_4$, $H_2O$. Use of $H_2$ as gas can be considered advantageous when applied in processes where the next phase also requires the presence of hydrogen, such as HDO. Then $H_2$ may flow through the reactor into said next phase. The most preferred gas is $CO_2$ as this is the product gas and may be efficiently recycled back to the feed, and it provides the most selective ketonisation reaction. According to a preferred embodiment, the ketonisation reaction conditions comprise the presence of $CO_2$ gas flow, preferably $CO_2$ flow from 0.25 to 1 gas/feed (w/w)).

The alcohol used for esterification reaction of the fatty acid esters, provides a corresponding alkene in the ketonisation reaction. This has now been surprisingly found to provide an alkene reagent usable in the metathesis reaction. Hence, when ethanol is reacted with fatty acids to produce esters, the ethene released correspondingly from ketonisation of two esters can be recycled back to metathesis reaction. The same applies to use of propanol, which yields propene from ketonisation.

Hydrotreatment

Hydrotreatment refers to reactions in the precence of hydrogen such as hydrodeoxygenation (HDO), hydrogenation of double bonds, hydrocracking and/or hydroisomerisation, and it may also remove some metals. Within the context of the present process, hydrotreatment is needed for olefinic bond saturation and for removal of covalently bound oxygen from the fatty acid esters and from ketones. Typically, this means deoxygenation by hydrogenation i.e. hydrodeoxygenation (HDO) and hydrogenation of double bonds. Preferably, hydrotreatment comprises both hydrodeoxygenation and hydroisomerisation.

Hydrodeoxygenation

Hydrodeoxygenation of the fatty acid esters, optional fatty acids and ketones may be carried out as depicted e.g. in EP1741768A1, WO2007068795A1, WO2016062868A1 or EP2155838B1, using a conventional hydrotreatment catalysts and hydrogen gas.

In one embodiment the hydrodeoxygenation takes place at reaction conditions comprising a temperature in the range from 100 to 500° C., preferably from 250 to 400° C., more preferably from 280 to 350° C., most preferably at temperature of 300-330° C.; and at a pressure in the range from 0.1 to 20 MPa, preferably from 0.2 to 8 MPa. Preferably, the weight hourly space velocity (WHSV) is in the range from 0.5 to 3.0 $h^{-1}$, more preferably from 1.0 to 2.5 $h^{-1}$, most preferably from 1.0 to 2.0 $h^{-1}$. Preferably, $H_2$ flow is in the range from 350 to 900 nl $H_2$/l feed, more preferably from 350 to 750, most preferably from 350 to 500, wherein nl $H_2$/l means normal liters of hydrogen per liter of the feed into the HDO reactor, in the presence of a hydrodeoxygenation catalyst. The hydrodeoxygenation catalyst is preferably selected from Pd, Pt, Ni, Co, Mo, Ru, Rh, W, or any combination of these, such as CoMo, NiMo, NiW, CoNiMo on a support, wherein the support is preferably alumina and/or silica, preferably, CoMo or NiMo on alumina support.

Isomerisation (Hydroisomerisation)

Isomerisation can be carried out in a conventional hydroisomerisation unit, such as those depicted in EP1741768A1, WO2007068795A1, WO2016062868A1 or EP2155838B1. Hydrogen is added into the isomerisation step.

Both the hydrodeoxygenation step and hydroisomerisation step may be conducted in the same reactor, and even in the same reactor bed or in separate reactors and/or separate beds. The hydroisomerisation catalyst may be a noble metal bifunctional catalyst such as a Pt containing commercial catalyst, for example Pt-SAPO or Pt-ZSM-catalyst or for example a non-noble catalyst, such as NiW. The hydrodeoxygenation and hydroisomerisation steps may be performed using NiW catalyst, or even in the same catalyst bed using the NiW catalyst for both the hydrodeoxygenation and isomerisation. The NiW catalyst may additionally result in more hydrocracking to diesel and naphtha products.

The hydroisomerisation step is preferably performed at a temperature from 250 to 400° C., more preferably from 280 to 370° C., most preferably from 300 to 350° C. Pressure is preferably from 1 to 6 MPa, more preferably from 2 to 5 MPa, most preferably from 2.5 to 4.5 MPa. The WHSV is preferably from 0.5 to 3 1/h, more preferably from 0.5 to 2 1/h, most preferably from 0.5 to 1 1/h, and $H_2$ flow from 100 to 800, more preferably from 200 to 650, most preferably from 350 to 500 n-liter $H_2$/liter feed, wherein n-liter $H_2$/l means normal liters of hydrogen per liter of the feed into the isomerisation reactor.

During hydroisomerisation n-paraffins are branched i.e. forming i-paraffins. Preferably, the conditions are chosen such that the branches are located at or near the terminal ends of the molecules, and therefore the cold flow properties of renewable base oil or optional renewable fuels are improved.

According to an embodiment, the third fatty acid ester fraction recovered from separation in step d comprising of fatty acid esters having a carbon chain length of C18-C20 is subjected to hydrotreatment to produce a saturated hydrocarbon stream comprising i-paraffins and n-paraffins. The fraction comprises both C18:0 and C18:1 residues. Preferably the processing further comprises fractionation of the saturated hydrocarbon stream into least one component selected from renewable base oil, renewable diesel, renewable naphtha component, and renewable gasoline. Compared to the prior art processes using triglycerides for production of renewable fuels, such fraction consumes considerably less hydrogen, because it is predominantly saturated and does not contain glycerol.

When performing renewable base oil production through ketonisation step, the following hydrotreatment is preferably adapted to this particular stream. Preferably hydrotreatment is conducted as hydrodeoxygenation and hydroisomerisation, either as a sequence or together in one step. It may be desirable to reduce the severity of the hydroisomerisation reaction to avoid or to reduce the amount of cracking of the renewable base oil product by selecting suitable combinations from the temperature, pressure WHSV and $H_2$ flow ranges of temperature from 250 to 400° C.; pressure is from 1 to 6 Mpa; the WHSV is from 0.5 to 3 1/h; and $H_2$ flow n-liter $H_2$/liter feed from 100 to 800.

According to one embodiment, the fatty acid esters may be subjected to both hydrodeoxygenation reaction conditions and to hydroisomerisation reaction conditions, simultaneously or in sequence, to yield a deoxygenated and isomerized paraffinic product stream comprising components suitable as renewable fuel components. According to a preferred embodiment, the saturated hydrocarbon stream comprises paraffins in the range of carbon number C15-C18 at least 70 wt-%, preferably at least 80 wt-%, more preferably at least 90 wt-% of the total weight of saturated hydrocarbon stream.

Products

As one aspect of the present invention herein is provided a use of a glyceride containing feedstock for production of at least base oil. The ketonisation and hydrotreatment yield a renewable base oil meeting the API group III specifications, more specifically a renewable base oil fulfilling the API Group III base oil specifications containing ≤0.03 wt-% sulfur, having a viscosity index of ≥120, having carbon numbers of at least C18, containing at least 90%-wt of saturated hydrocarbons, the saturated hydrocarbons consisting of paraffinic and naphthenic compounds and contains based on FIMS analysis mononaphthenes from 1 to 6%-wt. As to structure, preferably said base oil comprises of C31 paraffins.

The reference "renewable" in relation to the products obtainable from the present process, refers to high renewable carbon content in the products. Typically, renewable carbon predominates that of fossil origin. In specific cases, all carbon of a product may be of renewable origin. However, it is generally accepted that some reagents, such as hydrogen, used in the processes may originate from non-renewable sources and yet the product is considered renewable. The renewable content may be determined from both the starting materials and the products, i.e. by isotopic distribution involving $^{14}C$, $^{13}C$ and/or $^{12}C$ as described in ASTM D6866. According to the present disclosure the renewable products obtained, such as diacids, have a $^{14}C$ concentration of the total carbon content that is clearly measurable and distinct from that of fossil products, preferably more than 50 wt-%, more preferably more than 90 wt-%, most preferably more than 98 wt-%, such as 99 wt-% or higher.

In addition, further renewable chemicals are recovered from the process. Further products obtainable by the present process can be characterized as renewable fuel components, such as renewable diesel, naphtha and gasoline fuel components. Such components are used as such or in blends providing products fulfilling specifications set for said products.

The fraction recovered from metathesis product separation comprising or consisting essentially C10-C12 alkenes may be used for lubricant or special chemicals' manufacture, such use as cleaning agents, as disclosed in US 2016/0340616 A1. The C10 fraction that is essentially 1-decene can be used in preparation of PAO lubricants. Depending on the reagent used in the metathesis reaction, a double bond is typically at alpha, beta or gamma position. Metathesis products recoverable from separation comprise 1-decene, 3-dodecene, 1,4-decadiene, 3,5-dodecadiene, dependent on the starting materials.

In the metathesis feed, an abundant reacting fatty acid ester is 018:1, thus alkyl oleate. When using ethene as metathesis reagent, the most interesting C10 alkene fraction comprises 1-decene, and some 1,4-decadiene and 1,4,7-decatriene. When using propene or 2-butene as metathesis reagent, the recovered C11 alkene fraction comprises 2-undecene, and some 2,5-undecadiene and 2,5,8-undecatriene. With propene, the C10 fraction is equally present. Respectively, when using 1-butene as metathesis reagent, the main product is recovered as C12 fraction comprising 3-dodecene. Further, with 1-butene, the C10 fraction is again equally present.

Polyunsaturated fatty acid alkyl esters produce shorter alkenes as well.

The fatty acid ester fraction comprising or consisting essentially of unsaturated fatty acid esters having a carbon chain length of C10-C12 may be used for oleochemicals' manufacture such as for fatty alcohols, soaps, dimer acids, esters, amides, amines, sulfonates, etc.

With regard to fatty acids as metathesis products, the products formed from alkyl oleate are especially interesting. With ethene as metathesis reagent, the C10 ester fraction is of interest, especially 9-decenoate. When using propene or 2-butene as metathesis reagent, the prevailing fraction is C11 and therein 9-undecenoate. Respectively, when using 1-butene as metathesis reagent the C12 ester fraction and 9-dodecenoate are the main products. All said reagents, except 2-butene produce C10 esters. The fatty acid esters recoverable from metathesis comprise unsaturated fatty acid esters having thus varying carbon chain lengths. Many C10-C12 fatty acid esters may be used for oleochemicals' manufacture such as for fatty alcohols, soaps, dimer acids, esters, amides, amines, sulfonates, etc.

Polyunsaturated fatty acid alkyl esters produce longer metathesis product fatty acid esters, such as linoleic acid (C18:2) with ethene a C13-ester fraction, with propene a C14-ester fraction etc.

Products with terminal a C=C double bond are most desired. Further, monounsaturated fatty acid esters are preferred over polyunsaturated products.

In the prior art, use of C10-C12 esters as solvents or as components in cleansing solutions for petroleum fluids and deposits is disclosed in WO 2015/108874 A1. When reacted with alkenes, they have applications as lubricants (U.S. Pat. No. 9,676,884 B2). When polymerized, they can be used as dispersants or detergents (WO 2012/129477 A1). If they are transesterified with polyols, hydraulic fluids can be prepared (WO 16014417 A1). Other reactions of the ester group can give for example degreasers, laundry detergents, emulsifiers, dispersants for agricultural formulations, personal cleansing agents, oil recovery enhancers, corrosion inhibitors, emulsion polymerisation surfactants (US 2015/0087521 A1, WO 2012/061093 A1, US 2013/0225409 A1, US 2013/0225473 A1, US 2014/0005423 A1). If esters are converted to free acids, estolide lubricants can be prepared from them (U.S. Pat. No. 8,580,985 B2).

The third fatty acid ester fraction comprising or consisting essentially of fatty acid esters having a carbon chain length of C18-C20 is used as precursors for oleochemicals. C18-C20 esters can be used as fuel components (FAME) or lubricating agents. They are also suitable feedstock in the preparation of soaps and candles. Further, fatty acid esters having a carbon chain length of C18-C20 may be subjected to ketonisation and hydrotreatment as described earlier for the palmitates for production of base oils comprising paraffins having carbon numbers from C35 to C39.

According to a preferred embodiment, the present process through its different branches provides combined renewable products, hence renewable alkenes, renewable oleochemicals and renewable base oil, and optionally renewable paraffinic fuels.

The renewable content for any renewable product herein may be determined from both the starting materials and the products by isotopic distribution involving $^{14}C$, $^{13}C$ and/or $^{12}C$ as described in ASTM D6866 (2018).

The hydrodeoxygenation, isomerisation or combination thereof provides renewable paraffinic fuel components as products. The term "renewable paraffinic fuel component" defines said products being saturated hydrocarbons suitable for use as components for certain fuel grades. Paraffinic refers to their character as alkanes, straight chain or branched, not containing heteroatoms or double bonds.

The present processes may be described with reference to Figures.

FIG. 1 outlines as a schematic presentation of the process of the present invention for producing renewable base oil and chemicals. In FIG. 1 the glyceride containing feedstock 101 comprising free fatty acids, fatty acid glycerides selected from monoglycerides, diglycerides and triglycerides of fatty acids, or a mixture thereof including a compound having at least one carbon-carbon double bond, is directed to an esterification reaction 100. The esterification reaction may be an esterification of the free fatty acids of the feed or transesterification of the glycerides. The esterification reaction 100 takes place in the presence of a C2-C4 monoalcohol 102 introduced into the esterification reaction 100 to yield a fatty acid ester containing stream 104 and a residue 103 containing water and optional alcohols, such as unreacted C2-C4 monoalcohol, glycerol released from glycerides or a combination thereof. The fatty acid ester containing stream 104 is directed to metathesis reaction 110. In the presence of a C2-C4 alkene the fatty acid ester reacts providing metathesis product 105 comprising a mixture of alkenes and fatty acid esters. The composition of metathesis product 105 is dependent on the fatty acid ester(s) of stream 104, the C2-C4 alkene and metathesis reaction conditions. The obtained metathesis product 105 is subjected to separation 120 to provide at least a first fatty acid ester fraction 106 comprising saturated fatty acid esters having a carbon chain length of C16 in an amount of at least 80%-wt of the total weight of the product 105. This first fatty acid ester fraction 106 is used as feed in a renewable base oil manufacture by subjecting it to ketonisation 130 to yield an alkene 108 i.e. ethene, propene or butenes, preferably ethene, and a ketonisation product 107 comprising a C31 ketone. The ketonisation product 107 is further hydrotreated in a hydrotreatment step 140, and optionally isomerized, to obtain renewable base oil product 109 fulfilling the API Group III base oil specifications, having >90 wt-% saturated hydrocarbons, ≤0.03 wt % sulfur and a viscosity index of ≥120. The alkene 108 obtained during the ketonisation 130 is reused by recycling it back to the metathesis reaction 110 and thus decreasing, or even removing, the need for fresh alkene introduction into the metathesis reaction.

Figure 2:
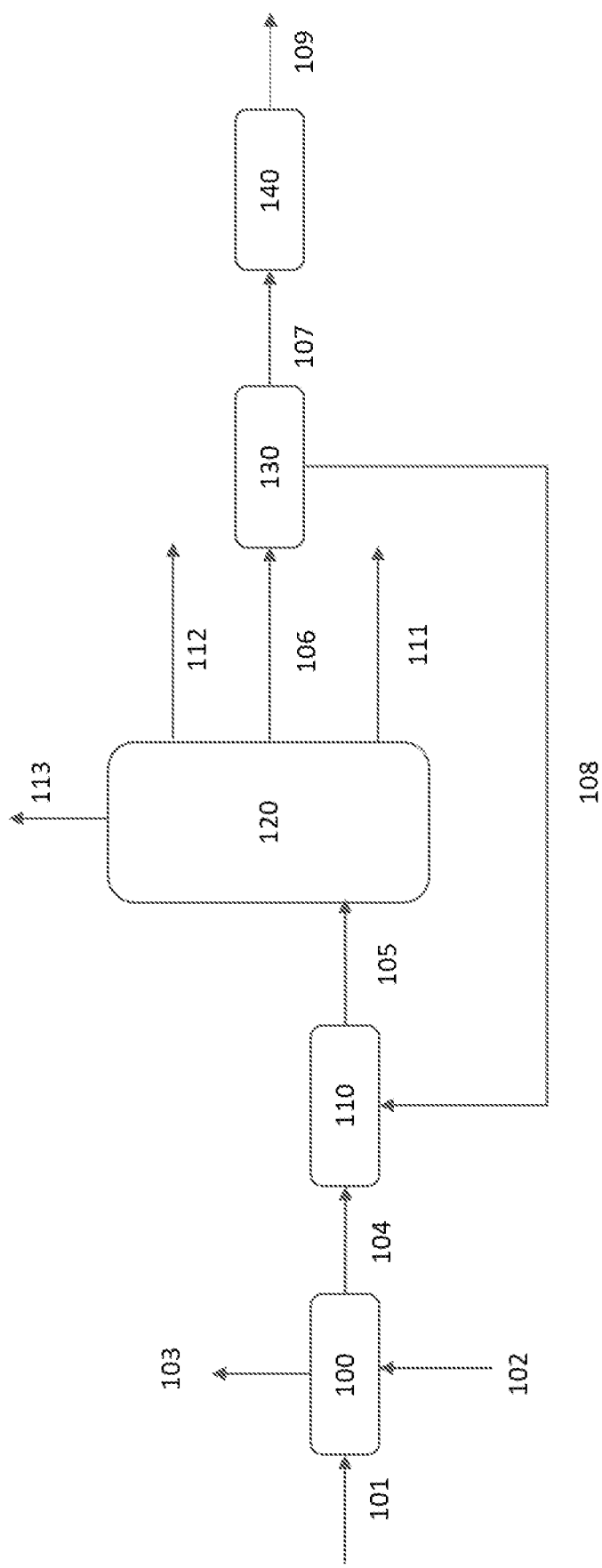
FIG. 2 shows a schematic arrangement of another embodiment of the present process as a flowchart following the stepwise structure of the process of claim 3.
Figure 3:
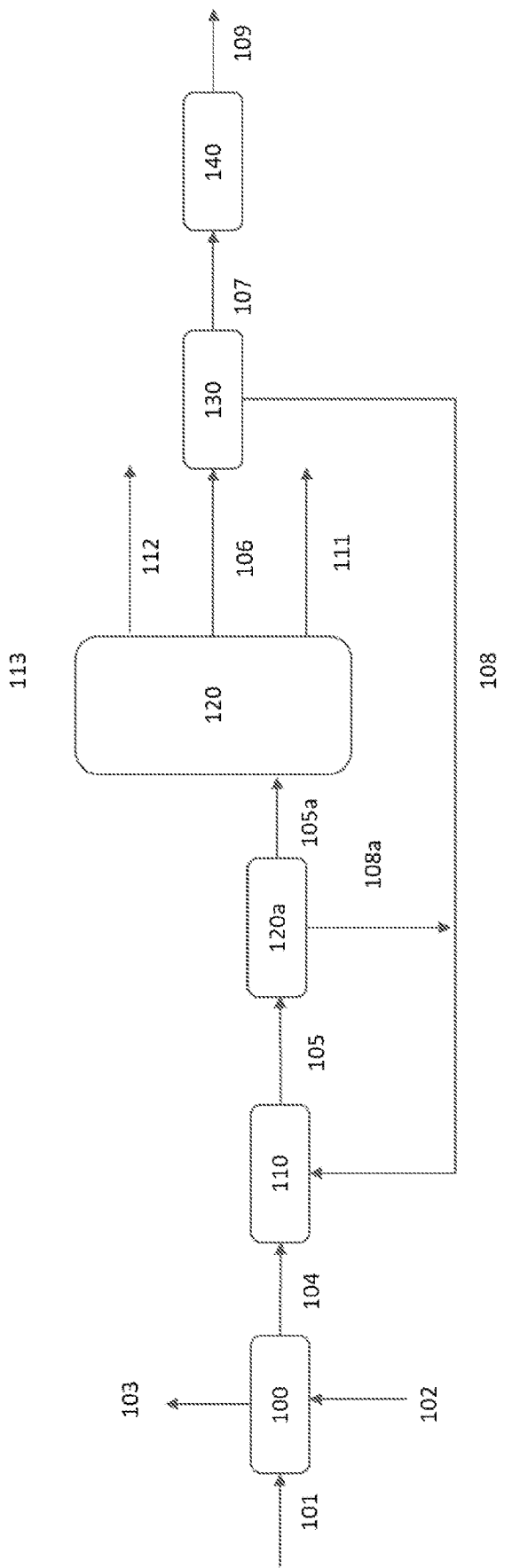
FIG. 3 shows a schematic arrangement of an embodiment of the present process as a flowchart further comprising a reagent recovery and recycle from metathesis reaction.

FIGS. 2 and 3 depicts embodiments of the present process for obtaining multiple renewable products.

The glyceride containing feedstock 101 is directed to an esterification reaction 100 similarly to FIG. 1. The esterification reaction 100 takes place in the presence of a C2-C4 monoalcohol 102 introduced into the esterification reaction 100 to yield a fatty acid ester containing stream 104 and a residue 103 containing water and optional alcohols, such as unreacted C2-C4 monoalcohols, glycerol released from glycerides or a combination thereof.

The fatty acid ester containing stream 104 is directed to metathesis reaction 110. In the presence of a C2-C4 alkene the fatty acid ester reacts into a product 105 comprising a mixture of alkenes and fatty acid esters. These alkeness and fatty acid esters include at least C10-C12 alkenes, unsaturated fatty acid esters having a carbon chain length of C10-C12, along with unreacted saturated C16 fatty acid esters and fatty acid esters having a carbon chain length of C18-C20. For example, unsaturated oleic acid ethyl esters of the feed may be split by ethene to 1-decene and ethyl-9-decenoate while the saturated fatty acid esters pass the metathesis reactor unreacted. The obtained product 105 is subjected to separation 120.

FIG. 3 provides a more detailed description of the separation depicting evaporation 102a separating from the metathesis product 105 the lightest alkenes, C2-C4 alkenes 108a, such as metathesis reagent, to be recycled to 110, and providing the light alkene depleted metathesis products 105a the separation 120. separation 120, preferably by fractional distillation, yields at least a first fatty acid ester fraction 106 comprising saturated fatty acid esters having a carbon chain length of C16 in an amount of at least 80%-wt of the total weight of the metathesis product 105. In addition of the fraction 106, at least one further fraction selected from a fraction 113 comprising or consisting essentially C10-C12 alkenes, a fatty acid ester fraction 112 comprising or consisting essentially of unsaturated fatty acid esters having a carbon chain length of C10-C12, and fatty acid ester fraction 111 comprising or consisting essentially of fatty acid esters having a carbon chain length of C18-C20 is obtained. The fraction 106 is used as feed to a renewable base oil manufacture by subjecting it to ketonisation 130 to yield an C2-C4 alkene 108 i.e. ethene, propene or butenes, preferably ethene, and a ketonisation product 107 comprising a C31 ketone. The ketonisation product 107 is further hydrotreated in a hydrotreatment step 140, and optionally isomerized, to obtain renewable base oil 109 product fulfilling the API Group III base oil specifications, having >90 wt-% saturated hydrocarbons, ≤0.03 wt % sulfur and a viscosity index of ≥120. The alkene 108 obtained during the ketonisation 130 is reused by recycling it back to the metathesis reaction 110 and thus decreasing, or even removing, the need for fresh alkene introduction into the metathesis reaction. The fraction 113 comprising or consisting essentially C10-012 alkenes may be used for lubricant or special chemicals' manufacture. Whereas, the fatty acid ester fraction 112 comprising or consisting essentially of unsaturated fatty acid esters having a carbon chain length of C10-C12 may be used for oleochemicals' manufacture such as for fatty alcohols, soaps, dimer acids, esters, amides, amines, sulfonates, etc. The fatty acid ester fraction 111 comprising or consisting essentially of fatty acid esters having a carbon chain length of C18-C20 may be used as feed for the renewable diesel fuel production by subjecting it to hydrotreatment, preferably to hydrodeoxygenation and optionally to isomerisation.

Another aspect of the invention, providing a use of renewable ethene as reagent for metathesis reaction can be followed with the aid of FIG. 3. Said ethene, as an example of a C2-C4 alkene 108 is recovered from the ketonisation reaction 130 of fraction 106 of fatty acid ethyl esters. Further, ethene as an C2-C4 alkene, is recovered 108a from metathesis products and recycled back to the metathesis reactor. In the figure, stream 108a from evaporator 120a is combined with stream 108 from the ketonisation 103, which are fed to metathesis.

EXAMPLES

A glyceride containing feedstock in the present example was palm oil fatty acid distillate (PFAD).

Esterification

The feedstock was first subjected to esterification reaction of fatty acids in the presence of ethanol. Reaction was conducted at conditions common for esterification. A fatty acid ester containing stream was obtained, having ethyl ester distribution depicted in Table 2, measured by analyses of liquid products run on GC.

TABLE 2

| Ester | wt-% |
| --- | --- |
| Ethyl myristate (C14:0 Et) | 1.2 |
| Ethyl palmitate (C16:0 Et) | 46.4 |
| Ethyl oleate (C18:1 Et) | 35.6 |
| Ethyl linoleate (C18:2 Et) | 9.1 |
| Ethyl stearate (C18:0 Et) | 4.3 |
| Ethyl linolenate (C18:3) | 0.3 |
| Others | 3.1 |

The ester mixture was purified by triethylaluminium pretreatment (see for example paragraphs [0080-86] of US 2014275595 A1).

Metathesis

The mixture of Table 2 (1000 g) and a metathesis catalyst solution were loaded under nitrogen atmosphere to a stainless-steel reactor equipped with a magnetic stirrer, pressure and temperature measurement, a sampling tube and a gas inlet. The catalyst used was a commercially available metathesis catalyst, which was used in an amount instructed by the provider. The reactor was closed and pressurized with 6 barg of ethene. Optionally the pressure may be provided with a gas inert to the metathesis and ethene fed only in amounts needed for the reactions. Vigorous mixing was started and temperature was increased to 50° C. The pressure was kept constant by feeding more ethene to replace that reacted. After 18 hours the reactor contents were analyzed with GC. The conversion of O18:1 Et was 83%, C18:2 Et 98% and C18:3 Et 100%. The composition is shown in Table 3.

TABLE 3

Ethenolysis reaction products are referred to as Cxx:y, wherein xx provides the carbon number of the fatty acid part of the ester and y the number of double bonds therein. Et refers to ethyl, hence compounds are ethyl esters accordingly, for example, C10:1 Et refers to ethyl 9-decenoate. Alkenes (olefins) formed in reactions with ethene are predominantly α-olefins, and are here characterized by their carbon chain length only.

| | wt-% |
| --- | --- |
| C14:0 Et | 1.2 |
| C16:0 Et | 44.8 |
| C10:1 Et | 20.5 |
| C10 olefins | 12.2 |
| C18:1 Et | 5.9 |
| C18:0 Et | 4.1 |
| C18:2 Et | 0.1 |
| C18:3 Et | 0.0 |
| Others | 11.2 |

The amount of C10:1 Et corresponds 1.07 mol and that of C10 olefins 0.91 mol. In theory the molar ratio should be 1:1. The "missing" 0.16 mol of C10 olefins is mainly caused by further splitting of 1,4-decadiene (formed from C18:2 Et) with ethene. From this we get a good approximation of the ethene consumption: 1.07 mol+0.16 mol=1.23 mol, corresponds 34.5 g ethene. In this case long reaction time was used to ensure that the reactions reach equilibrium. Metathesis reactions are often desirable to be stopped before the equilibrium is reached to optimize the catalyst utilisation. The products are isolated and the unreacted starting material is recycled back to metathesis.

First light hydrocarbons were removed by heating at ambient pressure, bp. 25-95° C. Then the primary metathesis products (C10 olefins and C10:1 Et) were removed by distillation at mbar, bp. 70-144° C. The fatty acid ester fraction (496 g) comprising 93.5 wt-% C16:Et was recovered at 15 mbar, bp. 175-195° C.

The C16:0 Et fraction thereby isolated, contained 1.76 mol fatty acid ethyl esters. This corresponds theoretical amount of 49.4 g ethene from the reaction

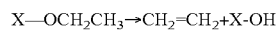

that seems to take place in the ketonisation step. This would be enough to provide all ethene that is consumed in the metathesis step. In practice it is possible that some additional ethene is needed.

Ketonisation

The equipment used to carry out the semi-batch ketonisation test was provided by 300 mL stirred reactor system from Parr Instrument Company. Heating, temperature, pressure, mixing speed and other process variables were managed with computer connected to Parr 4848B reactor controller. The main equipment consisted of 300 mL Hastelloy-made reactor, heater, stirrer motor and mixer, temperature and pressure sensors, safety rupture disk, heating cables and valves.

The reactor system was connected to three gas lines which were used in turns based on the type and phase of the experiment: the $CO_2$-bottle for ketonisation and He from gas manifold for pre-run leak testing. $CO_2$ and $H_2$ lines were connected into a gas measurement system to adjust the gas flow rate. The pressure in the reactor was adjusted and held stable with pressure valve allowing the water and $CO_2$ to flow out towards cooled water trap container. From this container, gas was led into Ritter drum-type gas volume meter and out of the fume hood by air exhaust.

Gas analysis was performed for the experiment product gas. The sample was collected for 4 hours involving the $CO_2$ fed into reactor and the $CO_2$ formed in the reactions. The method involves the analysis of inert gases: hydrogen, oxygen, nitrogen, carbon monoxide, and carbon dioxide as well as hydrocarbons from the carbon number area C1 to C6 with $Al_2O_3$ column or hydrocarbons from area C1 to C12 with non-polar column through gas chromatography.

Ketonisation of Ethyl Palmitate According to the Invention

Conditions applied for ethyl palmitate ketonisation are shown in table 4.

TABLE 4

| Reaction conditions of ethyl palmitate ketonisation | |
| --- | --- |
| Variable | value |
| Feed (ethyl palmitate) | 115 g |
| Catalyst ($TiO_2$, 0.15-0.35 mm) | 7.0 g |
| Temperature | 360° C. |
| Pressure | 20 bar |
| $CO_2$ flow | 1.0 L/h |
| Samples obtained during run | 4 |
| Total reaction time | ~5 hours |

Four samples were taken and analyzed by gas chromatography (GC). The results are shown in table 5.

TABLE 5

The conversion of ethyl ester of palmitic acid to ketones and alkene.

| Product | unit | Sample 1<br>1.1 h | Sample 2<br>3.1 h | Sample 3<br>4.0 h | Sample 4<br>4.3 h* |
|---|---|---|---|---|---|
| <C16:0 (Cracking, decarboxylation etc.) | wt-% | 5.3 | 11.3 | 13.4 | 14.0 |
| palmitic acid | wt-% | 40.8 | 12.7 | 5.1 | 2.7 |
| Feed: Ethyl palmitate | wt-% | 23.1 | 8.6 | 4.7 | 1.3 |
| Other Ketones | wt-% | 9.5 | 16.7 | 15.7 | 18.6 |
| Main product: C15-C15 ketone | wt-% | 20.4 | 48.2 | 58.3 | 59.5 |
| Heavies | wt-% | 0.8 | 2.4 | 2.9 | 3.9 |
| Total | wt-% | 100 | 100 | 100 | 100 |

*Last sample was taken from reactor after cooling (started at 4.0 h)

Main gas analyses are shown in table 6.

TABLE 6

Gas analysis results of hydrocarbons (ethyl ester test).

| Component | mol-% | wt-% |
|---|---|---|
| Methane | 0.3 | 0.1 |
| Ethene | 81.0 | 70.4 |
| Ethane | 7.3 | 6.8 |
| Propene | 0.3 | 0.4 |
| Butenes | 1.9 | 3.4 |
| Butane | 0.7 | 1.2 |
| Other alkenes | 1.1 | 2.2 |
| Ethanol | 1.0 | 1.4 |
| Diethyl ether | 4.0 | 9.2 |
| Other hydrocarbons | 2.4 | 4.9 |
| Total | 100.0 | 100.0 |

Table 6 shows that the major part of the organic gas formed (over 80 mol-%) is ethene (ethene), even though the reaction was not optimized. Ethene is the preferred co-product of the ketonisation of palmitic acid ethyl ester. Some ethanol and diethyl ether components are also observed which can also be converted to ethene or used as is, as fuel components. Butenes formed can be used as feed for alkylate, they are also e.g. excellent gasoline components produced at many crude oil refineries.

The invention claimed is:

1. A process for producing renewable base oil from a glyceride containing feedstock, the process comprising:
    a) providing a glyceride containing feedstock containing free fatty acids, and fatty acid glycerides selected from monoglycerides, diglycerides and triglycerides of fatty acids, or a mixture thereof, wherein the feedstock contains a compound having at least one carbon-carbon double bond;
    b) subjecting the feedstock to an esterification reaction, in a presence of a C2-C4 monoalcohol, to yield a fatty acid ester containing stream;
    c) subjecting said fatty acid ester containing stream to metathesis reaction conditions in a presence of a C2-C4 alkene to obtain a product having a mixture of alkenes and fatty acid esters,
    d) subjecting the product from step c) to separation to provide at least a first fatty acid ester fraction containing saturated fatty acid esters having a carbon chain length of C16 in an amount of at least 80%-wt of a total fraction weight;
    e) subjecting the first fatty acid ester fraction to ketonisation to yield C2-C4 alkene, and a ketonisation product containing a C31 ketone;
    f) recycling the C2-C4 alkene, from step e) to metathesis reaction in step c); and
    g) subjecting the ketonisation product of step e) to hydrotreatment to obtain renewable base oil fulfilling API Group III base oil specifications, having ≥90 wt % saturated hydrocarbons, ≤0.03 wt % sulfur and a viscosity index of ≥120.

2. A process according to claim 1, wherein the separation in step d) comprises:
    fractional distillation.

3. A process according to claim 2, wherein:
    the subjecting step b) includes esterification of fatty acids and transesterification of mono- di- or triglycerides or a combination thereof; and
    the separation in step d) provides at least one further fraction selected from:
    a fraction containing or consisting essentially of C10-C12 alkenes;
    a second fatty acid ester fraction containing or consisting essentially of unsaturated fatty acid esters having a carbon chain length of C10-C12; and/or
    a third fatty acid ester fraction containing or consisting essentially of fatty acid esters having a carbon chain length of C18-C20; and/or selected from esterification of fatty acids and transesterification of mono- di- or triglycerides or a combination thereof.

4. A process according to claim 1, wherein the separation in step d) provides at least one further fraction selected from:
    a fraction containing or consisting essentially of C10-C12 alkenes;
    a second fatty acid ester fraction containing or consisting essentially of unsaturated fatty acid esters having a carbon chain length of C10-C12; and
    a third fatty acid ester fraction containing or consisting essentially of fatty acid esters having a carbon chain length of C18-C20.

5. A process according to claim 4, comprising:
    the third fatty acid ester fraction containing or consisting essentially of fatty acid esters having a carbon chain length of C18-C20 is used as precursors for oleochemicals.

6. A process according to claim 4, comprising:
    subjecting the third fatty acid ester fraction containing or consisting essentially of fatty acid esters having a carbon chain length of C18-C20 to ketonisation and hydrotreatment for production of base oils.

7. A process according to claim 4, comprising:
    subjecting the third fatty acid ester fraction containing or consisting essentially of fatty acid esters having a carbon chain length of C18-C20 to hydrotreatment to produce a saturated hydrocarbon stream comprising i-paraffins and n-paraffins.

8. A process according to claim 7, comprising:
fractionation of the saturated hydrocarbon stream into least one component selected from renewable diesel, renewable naphtha component, and renewable gasoline.

9. A process according to claim 1, wherein the process comprises:
an evaporation after metathesis to recover C2-C4 alkenes.

10. A process according to claim 1, wherein the conditions of the ketonisation of step e) comprise:
a temperature from 300 to 400° C., and a pressure from 0.5 to 3 MPa, and a metal oxide ketonisation catalyst.

11. A process according to claim 1, wherein conditions of the ketonisation of step e) comprise:
a presence of a $CO_2$ gas flow, and/or a presence of a $CO_2$ flow of 0.25-1 gas/feed (w/w).

12. A process according to claim 1 comprising:
at least one pretreatment step between steps b) and c).

13. A process according to claim 12, wherein the pretreatment step comprises:
treatment with an adsorbent, with a metal alkyl compound, with a metal alkoxide compound, with a reducing agent, treatment with an organic drying agent, a thermal treatment and/or a combination thereof.

14. A process according to claim 1, wherein the monoalcohol used for esterification reaction of step b) is selected from ethanol, 1-propanol, 2-propanol, 1-butanol and 2-butanol, and/or a mixture thereof, and/or from bio based monoalcohols, and/or from bio-based ethanol.

15. A process according to claim 1, wherein the alkene in step c) is a same C2-C4 alkene as in step e), and/or methene.

16. A process according to claim 15, wherein metathesis products comprise:
1-decene and ethyl-9-decenoate.

17. A process according to claim 16, comprising:
polymerisation of 1-decene to renewable polyalphaolefin (bio-PAO).

18. The process according to claim 1, wherein the feedstock contains 17.7 wt % to 54.5 wt % of the compound having at least one carbon-carbon double bond, based on a total weight of the feedstock.

19. A process of a metathesis reaction, the process comprising utilizing a renewable C2-C4 alkene and/or renewable ethene, as a reagent for metathesis reaction.

20. The process according to claim 19, comprising:
recovering said renewable C2-C4 alkene from a ketonisation reaction of a fatty acid ethyl ester.

21. The process according to claim 20, wherein ketonisation reaction conditions comprise:
a temperature from 300 to 400° C., a pressure from 0.5 to 3 MPa, a metal oxide ketonisation catalyst, a presence of $CO_2$ gas flow, and/or a combination thereof.

* * * * *